(12) United States Patent
Stone (10) Patent No.: US 6,368,288 B2
(45) Date of Patent: Apr. 9, 2002

(54) ACOUSTIC COUPLING DEVICE

(75) Inventor: Robert T. Stone, Sunnyvale, CA (US)

(73) Assignee: Kinderlife Instruments, Inc., Mountain View, CA (US)

( * ) Notice: Subject to any disclaimer, the term of this patent is extended or adjusted under 35 U.S.C. 154(b) by 0 days.

(21) Appl. No.: 09/782,550

(22) Filed: Feb. 13, 2001

Related U.S. Application Data (60) Provisional application No. 60/182,279, filed on Feb. 14, 2000.

(51) Int. Cl.$^7$ ................................................. A61B 5/00
(52) U.S. Cl. ........................... 600/559; 181/129; 73/585
(58) Field of Search ........................... 600/559; 73/585, 73/587; 181/129, 130, 135; 381/56, 58, 104, 124, 328; 128/897

(56) References Cited

U.S. PATENT DOCUMENTS

| | | | | |
|---|---|---|---|---|
| 4,029,083 A | * | 6/1977 | Baylor | 600/559 |
| 4,677,679 A | * | 6/1987 | Killion | 381/74 |
| 4,930,520 A | | 6/1990 | Liverani | |
| 5,105,822 A | * | 4/1992 | Stevens et al. | 600/559 |
| 5,913,309 A | | 6/1999 | Sheehan et al. | |
| 5,916,174 A | * | 6/1999 | Dolphin | 600/559 |
| 5,923,764 A | * | 7/1999 | Shennib | 381/60 |
| 5,954,667 A | * | 9/1999 | Finkenzeller et al. | 600/544 |
| 6,129,174 A | * | 10/2000 | Brown et al. | 181/135 |
| 6,231,521 B1 | * | 5/2001 | Zoth et al. | 600/559 |

* cited by examiner

Primary Examiner—Kevin Shaver
Assistant Examiner—Charles Marmor, II
(74) Attorney, Agent, or Firm—Francis Law Group (57) ABSTRACT

An acoustic coupling device for a hearing screening device comprising engagement means being adapted to receive an acoustic stimulus from the hearing screening device and transmit at least one response signal from a subject (or patient) to the hearing screening device, stimulus monitoring means in communication with the engagement means for monitoring the acoustic stimulus, at least a first earpiece disposed proximate the cavity of at least one of said subject's ears having a stimulus input in communication with the engagement means adapted to receive the acoustic stimulus, the stimulus input being further adapted to receive and transmit the response signal from the subject to the engagement means, the earpiece further including a response signal output adapted to receive and transmit the response signal, and response signal monitoring means in communication with the response signal output for monitoring the response signal.

20 Claims, 5 Drawing Sheets

ACOUSTIC COUPLING DEVICE

CROSS REFERENCE TO RELATED APPLICATIONS

This application claims benefit under 35 U.S.C. 119 (e) of U.S. Provisional Application No. 60/182,279, filed Feb. 14, 2000.

FIELD OF THE INVENTION

The present invention relates generally to the field of audiometric devices and associated screening methods. More particularly, the invention relates to an acoustic coupling device for use in connection with equipment for stimulating the reaction to sound in a subject.

BACKGROUND OF THE INVENTION

Language acquisition in infants requires a critical period of hearing capacity, which spans the frequency range of human speech. The critical period extends from birth to about two to three years of age, when infants typically begin to talk with some level of proficiency.

Various hearing screening techniques have been developed over the years which present a sound input into the ear of a subject (i.e., infant) and detect a response to that input. The response is related to the characteristics of the sound input and the conditions inside the ear, the neural connections, and the vibration transmission mechanism of the ear.

In many instances, hearing screening is performed by using an earphone having a cavity that fits closely about the ear. Auditory tones or "clicks" are fed into the earphone cavity, and the response generated by the patient's ear and the neural conduction system in response to the auditory tones is sensed by a transducer. The transducer may be, for example, a microphone, suitable electrodes, piezo electric materials and like devices that generate signals representative of the response to the auditory input.

There are, however, several problems associated with the noted technique. A major problem is that ambient noises, internal or external to the cavity, are capable of interfering with the stimulus or the response signals and, hence, the results. In most cases, the monitoring equipment has mechanisms, such as microphones, for detecting and compensating for ambient background noise. Illustrative is the disposable earphone disclosed in U.S. Pat. No. 4,930,520 (Liverani), which is sold under the trademark Ear Couplers® by Natus Medical, Inc.

The Liverani earphone includes a toroidal baffle of anechoic, insulative foam, a clear planar window plastic sheet adhered to one side of the baffle defining a cavity, and an adhesive coating on the other side of the baffle for bonding the disposable earphone to the region surrounding the infant's ear. The earphone is employed with transducers for transferring acoustical energy through a pneumatic tube to the infant's ear for testing.

One of the problems with the Liverani device is that the earphone is somewhat cost-ineffective in that the entire earphone is not re-usable and must be disposed of after each use. Another problem with the device is that its construction is not capable of adjustment for infants with different size ears. As a result, it is necessary to manufacture different size earphones and maintain an inventory of the different sizes to obtain acceptable test performance for infants having different sized ears.

A further problem is that the Liverani device does not include any means for regulating or monitoring the amplitude of the stimulus presented to the infant.

In U.S. Pat. No. 5,913,309 a disposable earphone element is disclosed for use in hearing screening tests, which addresses some of the disadvantages associated with the Liverani device. The disposable element similarly includes an adhesive on one side of the element, which is adapted to adhere to the patient's skin around the ear. An adhesive is further provided on the opposite side of the element to temporarily adhere to the earphone. Thus, after a test is conducted, the disposable element is merely removed and replaced, allowing one to reuse the earphone.

Although the disposable element disclosed in the '309 eliminates the need to replace the entire earphone after each use, replacement of the disposable element is still somewhat cost-ineffective. Further, the disposable element does not include any means for regulating or monitoring the amplitude of the stimulus.

Finally, a problem associated with each of the noted devices is that the adhesive employed to adhere the devices to the skin is generally ineffective to maintain full contact with the infant during the period of hearing screening. Thus, ambient noise can, and in many instances will, enter into the cavity.

Accordingly, there remains a need for an improved acoustic coupling device that overcomes the problems of prior art devices and, further, provides means for regulating and/or monitoring the amplitude of the stimulus presented to the subject.

SUMMARY OF THE INVENTION

In accordance with the above objects and those that will be mentioned and will become apparent below, the acoustic coupling device (or apparatus) in accordance with this invention comprises engagement means adapted to engage a hearing screening device, the engagement means being adapted to receive an acoustic stimulus from the hearing screening device and transmit at least one response signal from a subject (or patient) to the hearing screening device, stimulus monitoring means in communication with the engagement means for monitoring the acoustic stimulus, at least a first earpiece disposed proximate the cavity of at least one of said subject's ears having a stimulus input in communication with the engagement means adapted to receive the acoustic stimulus, the stimulus input being further adapted to receive and transmit the response signal from the subject to the engagement means, the earpiece further including a response signal output adapted to receive and transmit the response signal, and response signal monitoring means in communication with the response signal output for monitoring the response signal.

In an additional embodiment of the invention the acoustic coupling device comprises engagement means adapted to engage said hearing screening device, the engagement means being adapted to receive a first acoustic stimulus from the hearing screening device and transmit at least one response signal from the subject to said hearing screening device, stimulus monitoring means in communication with the engagement means for monitoring the first acoustic stimulus, stimulus regulator means in communication with the stimulus monitoring means for providing a second acoustic stimulus in response to the first acoustic stimulus, at least a first earpiece disposed proximate the cavity of at least one of said subject's ears having a stimulus input in communication with the engagement means and the stimulus regulator means adapted to receive the second acoustic stimulus, the stimulus input being further adapted to receive and transmit the response signal to the engagement means, the earpiece further including a response signal output adapted to receive the response signal, and response signal monitoring means in communication with the response signal output for monitoring the response signal.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF PREFERRED EMBODIMENTS

The present invention substantially reduces or eliminates the disadvantages and drawbacks of prior art audiometric screening devices and systems. As discussed in detail below, in one embodiment of the invention the acoustic coupling device includes a plurality of multi-shaped, disposable ear pieces adapted to sealably engage a subject's ear canal (or cavity), monitoring means adapted to monitor at least the amplitude of the stimulus presented to the subject and the response signal emanating from the subject's ear(s), and engagement means adapted to facilitate the use of the invention on conventional hearing screening test devices. In an additional embodiment of the invention, the acoustic coupling device also includes regulator means adapted to control the stimulus presented to the subject.

Figure 1:
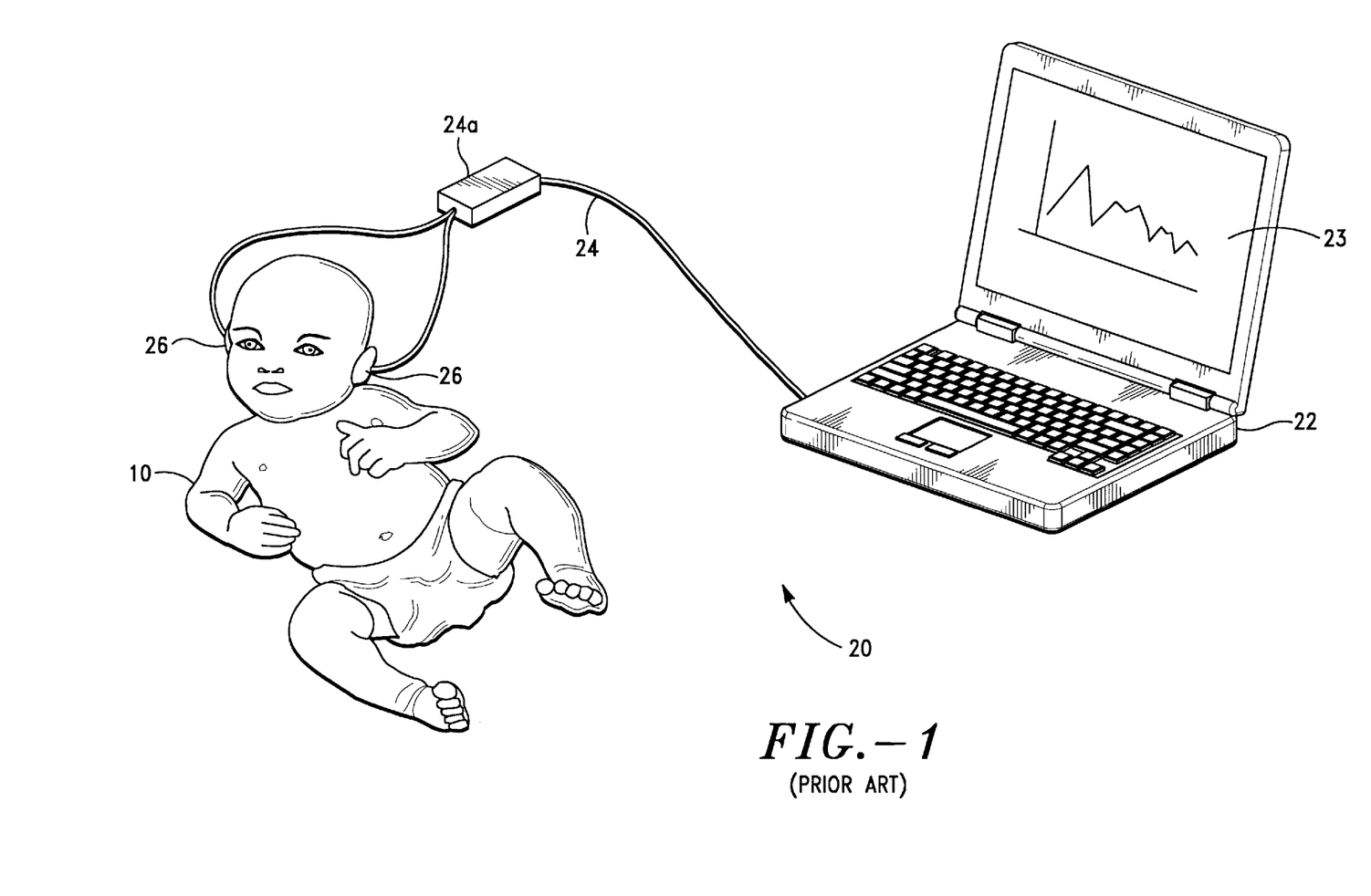
FIG. 1 is an illustration of a prior art hearing screening test device.

Referring first to FIG. 1, there is shown a prior art audiometric screening device (or system) 20. The device 20 includes a laptop computer 22 having a monitor 23 for displaying one or more characteristics of the processed signals emanating from the subject 10. The device 20 also includes means for providing at least one acoustic stimulus signal and means for receiving response signals from the subject 10.

The audiometric screening system 20 further includes a probe 24 having a pair of earphone assemblies 26, such as that disclosed in U.S. Pat. No. 5,826,582, for presenting the acoustic stimulus signal(s) to the subject 10. The earphone assemblies 26 are also adapted to receive the evoked otoacoustic emission (OAE) response signal from the subject's ear.

As discussed above, two major drawbacks of the noted device are (i) the earphone assemblies 26 must be replaced after each test and (ii) the earphone assemblies 26 do not include any means for monitoring or regulating the stimulus and, in particular, the amplitude of the stimulus presented to the subject 10.

Figure 2:
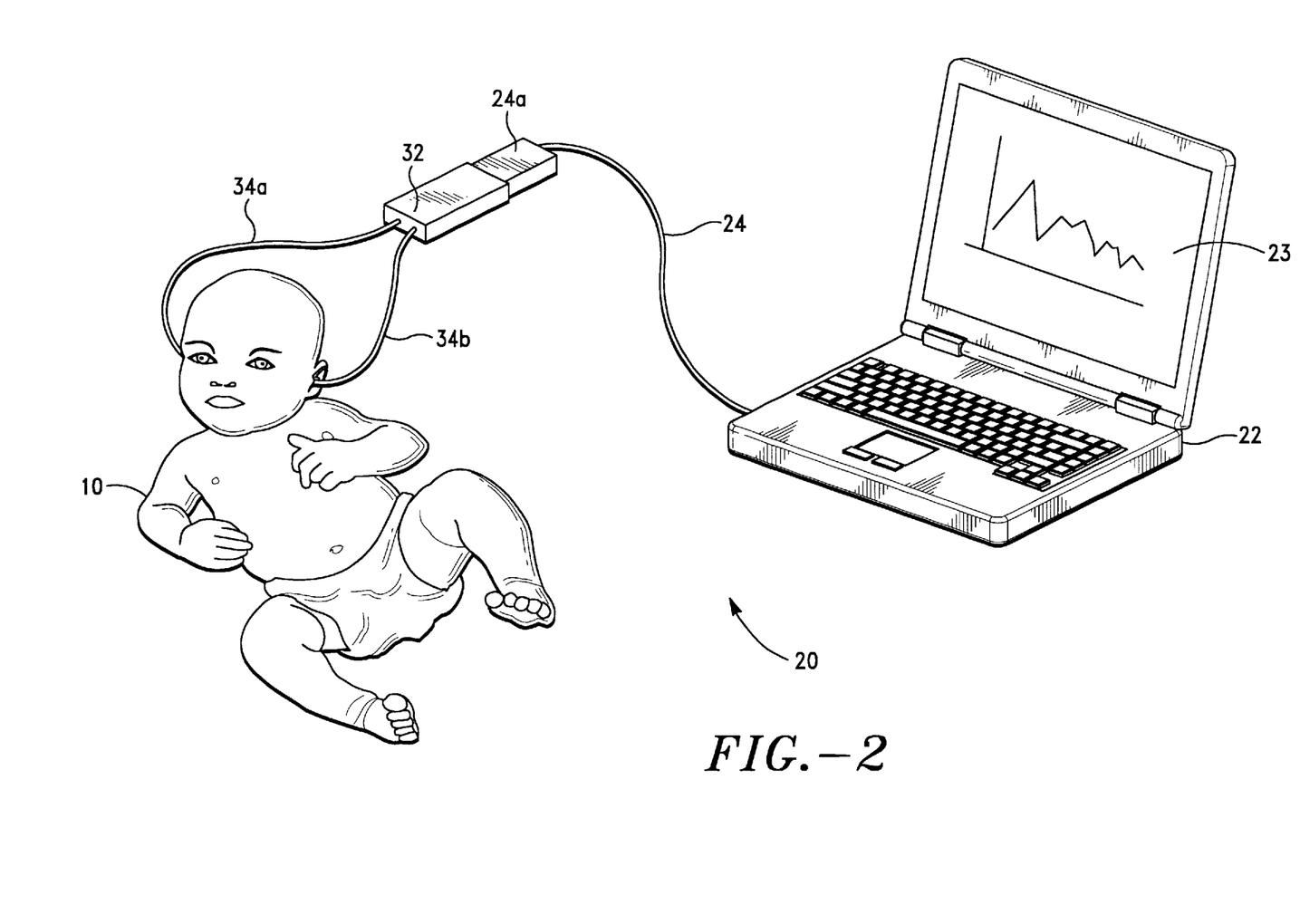
FIG. 2 is an illustration of the hearing screening device shown in FIG. 1 incorporating the acoustic coupling apparatus according to the invention.

Referring now to FIG. 2, there is shown one embodiment of the acoustic coupling device 32 of the invention incorporated into the device shown in FIG. 1. As illustrated in FIG. 2, the audiometric coupling device 32 is adapted to engage and, hence, communicate with the conventional audiometric device 20 via probe 24 (see also FIG. 3B).

Figure 3A:
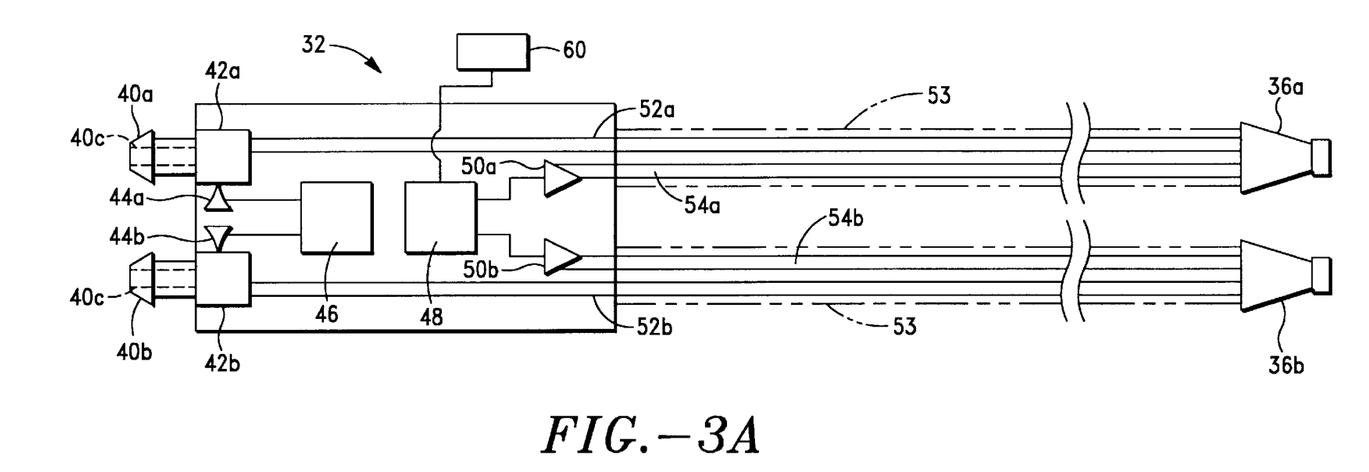
FIG. 3A is a schematic illustration of one embodiment of the acoustic coupling apparatus according to the invention.
Figure 3B:
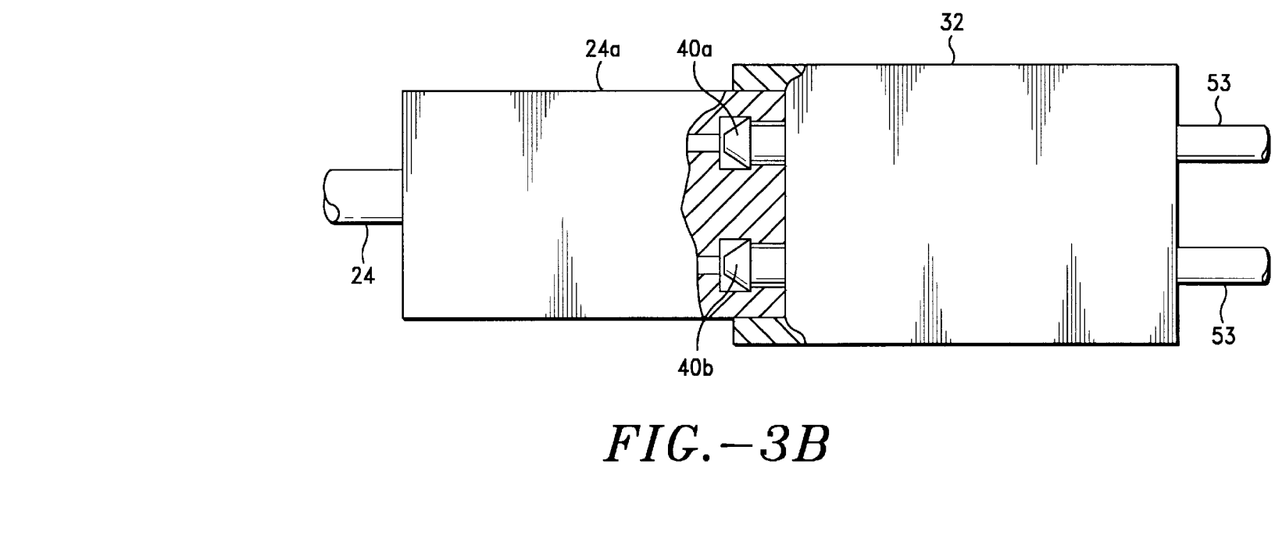
FIG. 3B is a schematic illustration of the acoustic coupling apparatus showing the engagement of the acoustic coupling apparatus to the hearing screening device according to the invention.

Referring now to FIG. 3A, there is shown a block diagram of a first embodiment of the acoustic coupling device 32. The coupling device 32 includes first and second inputs 40a, 40b having a lumen 40c therein adapted to receive and transmit the stimulus signal provided by the hearing screening device 20 to the subject 10 via leads 34a and 34b. As illustrated in FIG. 3B, the first and second inputs 40a, 40b are further adapted to slideably and substantially sealably engage the probe connector 24a.

As illustrated in FIG. 3A, the acoustic coupling device 32 further includes a pair of acoustic attenuators 42a, 42b in communication with inputs 40a, 40b. The attenuators 42a, 42b are preferably adapted to provide at least first and second reductions in stimulus (i.e., signal) amplitude, respectively. In a preferred embodiment of the invention, the first and second reductions in stimulus amplitude are substantially equal.

According to the invention, various attenuators 42a, 42b may be employed within the scope of the invention to provide the first and second reductions in stimulus amplitude. Such attenuators include conventional orifices, tubing lengths and other acoustic impedance devices, which are incorporated by reference herein.

Referring back to FIG. 3A, disposed on the opposing end of each attenuator 42a, 42b and in communication therewith are primary stimulus input leads or tubes 52a, 52b. Also disposed proximate each attenuator 42a, 42b are first and second microphones 44a, 44b. The microphones 44a, 44b are in communication with the coupling device control means 46, which is adapted to control the operation (e.g., activation) of the acoustic coupling device.

According to the invention, the microphones 44a, 44b are positioned and adapted to monitor the primary stimulus input (i.e., acoustic stimulus signal) presented to the attenuators 42a, 42b. Each of the microphones 44a, 44b are also preferably adapted to provide at least a first signal to the control means 46 indicative of the presence of the stimulus. In response to the first signal(s), the control means 46, in the instant embodiment, would activate the coupling device 32 (i.e., on/off switch).

Figure 5:
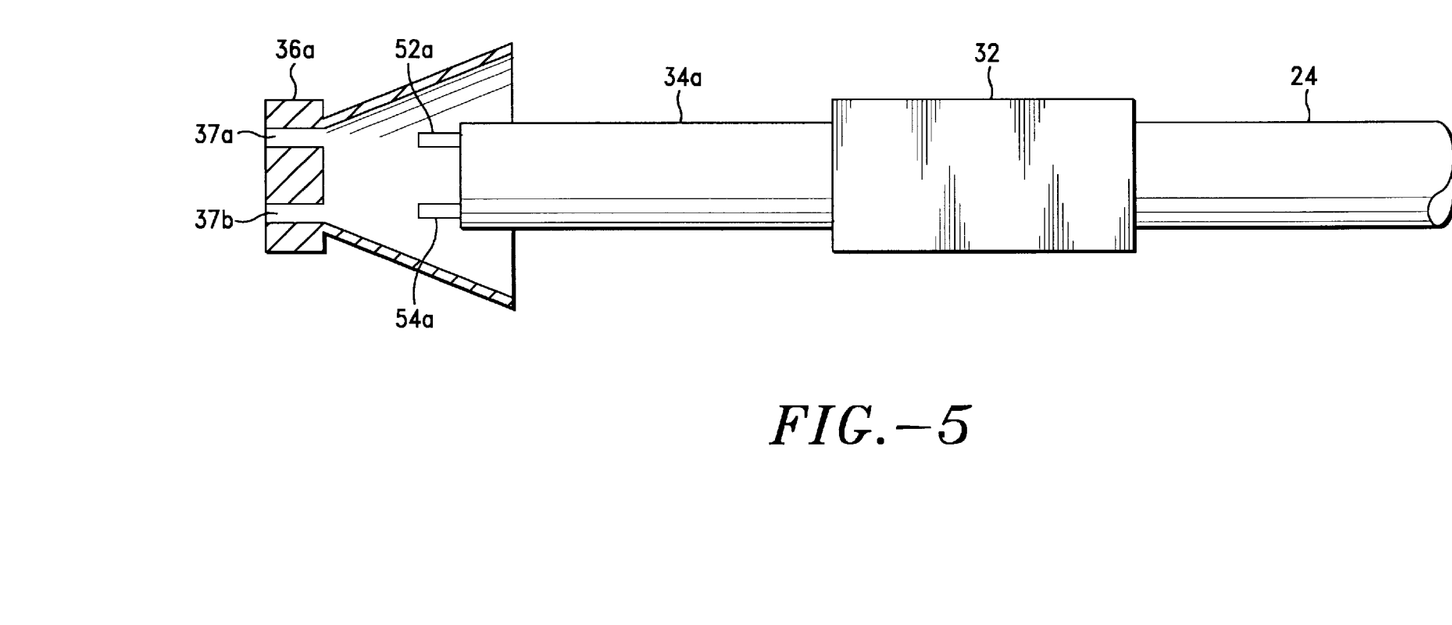
FIG. 5 is a sectional view of an earpiece according to the invention.

As illustrated in FIG. 3A, a first pair of input and output leads 52a, 54a, which are preferably encased in a cable housing 53 (shown in phantom), are in communication with a first earpiece 36a and a second pair of input and output leads 52b, 54b, which are similarly encased in a cable housing 53, are in communication with a second earpiece 36b. As illustrated in FIG. 5, each earpiece 36a, 36b is provided with an input and output lumen 37a, 37b adapted to slideably receive a respective one of the input 52a, 52b and output 54a, 54b leads.

In operation, a stimulus is presented to each of the subject's ears via input leads 52a, 52b and earpieces 36a, 36b. The stimuli are sensed and substantially simultaneously transmitted into and through leads 52a, 52b and communicated to microphones 50a, 50b via output leads 54a, 54b. The microphones 50a, 50b provide at least second and third signals in response to the detected (or response) stimuli, which are communicated to the monitoring means 48 of the invention.

According to the invention, the monitoring means 48 includes means for storing at least one stimulus amplitude indicative of an unacceptable response signal and means for comparing the unacceptable response signal to the response signal (i.e., detected stimulus or stimuli) from the subject 10. Various monitoring means, such as a conventional processor and comparator, may be employed within the scope of the invention. In a preferred embodiment, the monitoring means 48 comprises an A/D converter.

According to the invention, the monitoring means 48, in response to the second and third signals, is adapted to provide a plurality of signals, including at least a fourth signal indicative of an acceptable stimulus amplitude and a fifth signal indicative of an unacceptable stimulus amplitude.

In a preferred embodiment of the invention, at least one of the monitoring means signals are communicated to the coupling device display means 60. According to the invention, the display means 60 is adapted to provide a visual indication of the stimulus quality in response to the monitoring means signals.

As will be appreciated by one having skills in the art, various display means may be employed within the scope of the invention. In a preferred embodiment, the display means 60 comprises a conventional light emitting diode (LED) assembly.

Thus, by way of example, in response to the fourth signal referenced above, the display means 60 would illuminate a "green" light. In response to the fifth signal, the display means 60 would illuminate a "red" light.

Figure 4:
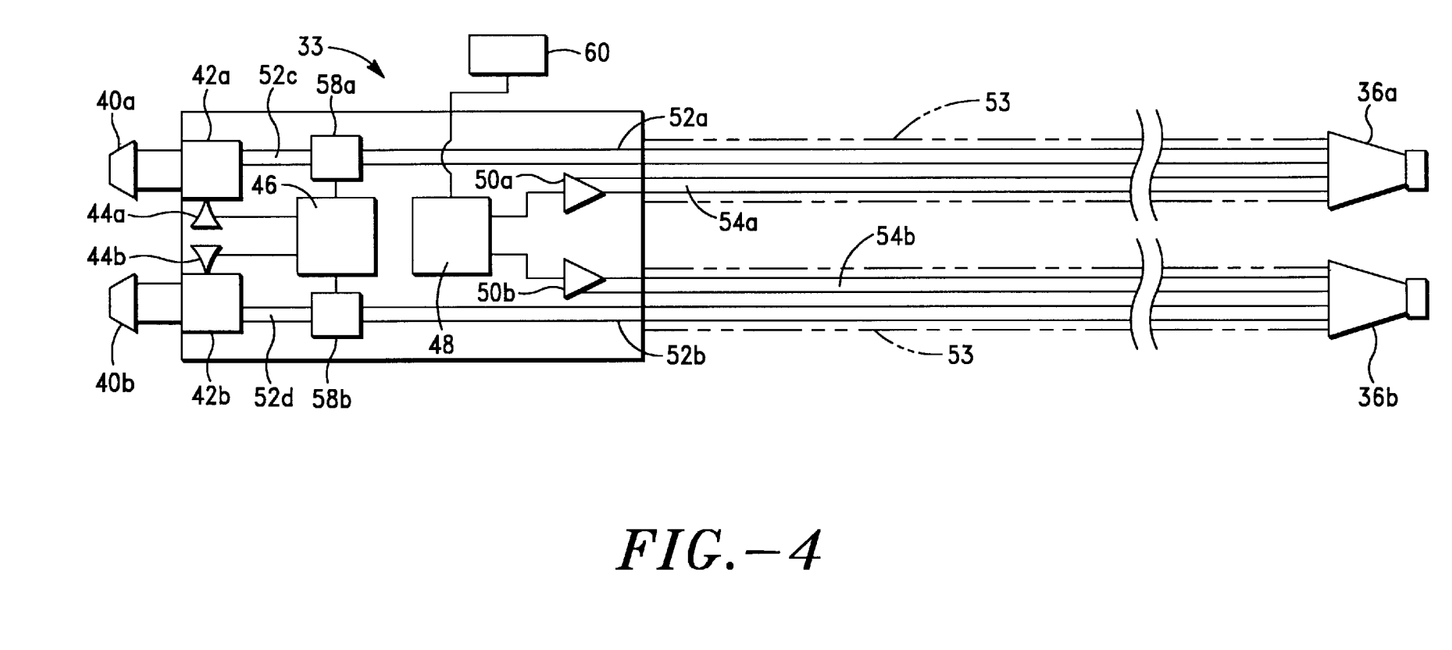
FIG. 4 is a schematic illustration of a further embodiment of the acoustic coupling apparatus according to the invention.

Referring now to FIG. 4, there is shown an additional embodiment of the acoustic coupling device, designated generally 33. In this embodiment, the device 33 further includes a pair of signal generators (or reproducers) 58a, 58b adapted to provide the desired amplitude of the stimulus.

As illustrated in FIG. 4, the signal generators 58a, 58b are in communication with the control means 46. According to the invention, the monitoring means 48 is also in communication with the control means 46. Thus, in operation, the monitoring means 48 would preferably provide at least sixth and seventh signals to the control means 46 indicative of the quality (or amplitude) of the stimulus signals detected by the microphones 50a, 50b, respectively. The control means 46, in response to the sixth and seventh signals, provides at least an eighth signal to signal generator 58a and at least a ninth signal to signal generator 58b. In response to the control means eighth and ninth signals, the signal generators 58a, 58b would increase or decrease the stimulus amplitude to an acceptable level.

As illustrated in FIG. 4, the signal generators 58a, 58b are in communication with input leads 52a, 52b. The signal generators 58a, 58b also include output leads 52c, 52d that are in communication with the first and second inputs 40a, 40b.

According to the invention, each of the noted audiometric coupling devices 32, 33 includes a pair of earpieces 36a, 36b that are adapted to be placed proximate or, more preferably, within the cavity of the subject's ear (i.e., one earpiece per ear) and engage the input and output leads 52a, 52b, 54a, 54b of the coupling device 32 (see FIG. 5). The earpieces 36a, 36b are preferably constructed out of a flexible polymeric material, such as low-density polyurethane.

As discussed, the earpieces 36a, 36b are provided with input and output lumens 37a, 37b that are adapted to slideably receive a respective one of the input 52a, 52b and output 54a, 54b leads. Thus, after use, the earpieces 36a, 36b can be readily removed and replaced.

Figure 6A:
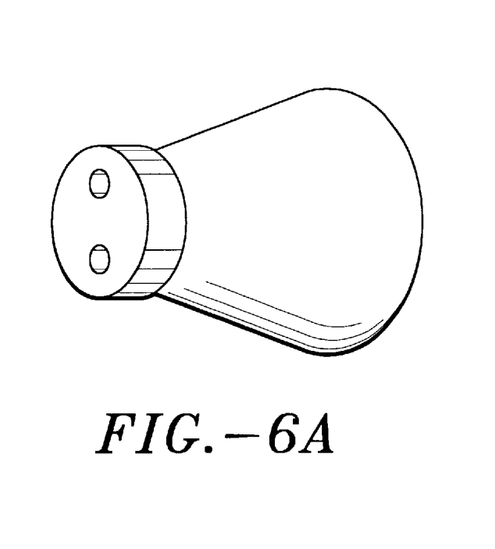
FIG. 6A is a perspective view of the earpiece shown in FIG. 5.
Figure 6B:
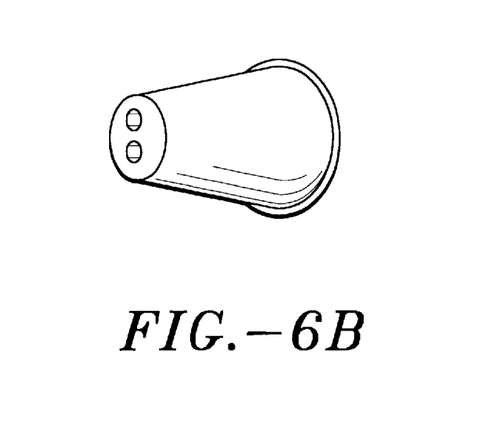
FIG. 6B is a perspective view of an additional embodiment of the earpiece according to the invention.

As will be appreciated by one having skill in the art, various configurations of the "low-cost" earpieces 36, such as the earpieces shown in FIGS. 6A and 6B, can be employed within the scope of the invention to provide an acceptable level of sealable engagement proximate the subject's ear canal.

It will be appreciated that the present invention may be employed with virtually all conventional hearing screening devices, such as the ALGO 1E™ and ALGO 2 hearing screening systems available from Natus Medical, as well as acoustic emission based systems.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An acoustic coupling apparatus for a hearing screening device adapted to test the hearing of a subject, said hearing screening device including means for providing a first acoustic stimulus and means for receiving a first response signal from the subject's first ear and a second response signal from the subject's second ear, comprising:

engagement means for substantially sealably engaging said hearing screening device, said engagement means including at least first and second input members in communication with said means for providing said first acoustic stimulus and means for receiving said first and second response signals, said first and second input members being adapted to receive and transmit at least said first acoustic stimulus and transmit at least said first and second response signals to said hearing screening device;

first monitoring means in communication with said engagement means for monitoring said first acoustic stimulus, said first monitoring means including at least a first acoustic attenuator in communication with said first input member and a second acoustic attenuator in communication with said second input member, said first attenuator being adapted to receive said first acoustic stimulus and provide at least a second acoustic stimulus in response to said first acoustic stimulus, said second attenuator being adapted to receive said first acoustic stimulus and provide at least a third acoustic stimulus in response to said first acoustic stimulus, said first attenuator including a first acoustic stimulus output adapted to transmit said second acoustic stimulus and said second attenuator including a second acoustic stimulus output adapted to transmit said third acoustic stimulus;

second monitoring means for monitoring at least said first response signal and second response signal, said second monitoring means including first response signal input means for receiving said first response signal and second response signal input means for receiving said second response signal, said second monitoring means including a first microphone in communication with said second monitoring means adapted to provide at least a first signal to said second monitoring means in response to said first response signal and a second microphone in communication with said second monitoring means adapted to provide at least a second signal to said second monitoring means in response to said second response signal; and a first earpiece adapted to be disposed proximate the cavity of said first ear and a second earpiece adapted to be disposed proximate the cavity of said second ear, said first earpiece including a first stimulus input in communication with said first acoustic stimulus output adapted to receive said second acoustic stimulus and said first response signal, said first earpiece further including a first response signal output adapted to receive at least said first response signal, said first response signal output being in communication with said first response signal input means, said second earpiece including a second stimulus input in communication with said second acoustic stimulus output adapted to receive said third acoustic stimulus and said second response signal, said second earpiece further including a second response signal output adapted to receive at least said second response signal, said second response signal output being in communication with said second response signal input means.

2. The apparatus of claim 1, wherein said second acoustic stimulus and said third acoustic stimulus have substantially equal amplitudes.

3. The apparatus of claim 1, wherein said first acoustic attenuator provides at least a first reduction in amplitude of said first acoustic stimulus and said second attenuator provides at least a second reduction in amplitude of said first acoustic stimulus.

4. The apparatus of claim 3, wherein said first and second reductions in amplitude of said first stimulus are substantially equal.

5. The apparatus of claim 1, wherein said apparatus includes control means for controlling at least the activation of said apparatus.

6. The apparatus of claim 5, wherein at least one of said first and second attenuators includes a third microphone to detect the presence of said first acoustic stimulus, said third microphone being adapted to provide at least a third signal to said control means in response to said presence of said first acoustic stimulus.

7. The apparatus of claim 1, wherein said second monitoring means provides at least a fourth signal in response to at least said first response signal indicative of an acceptable stimulus amplitude and at least a fifth signal in response to at least said first response signal indicative of an unacceptable stimulus amplitude.

8. The apparatus of claim 7, wherein said second monitoring means provides at least a sixth signal in response to at least said second response signal indicative of an acceptable stimulus amplitude and at least a seventh signal in response to at least said second response signal indicative of an unacceptable stimulus amplitude.

9. The apparatus of claim 8, wherein said apparatus includes display means in communication with said second monitoring means for providing a visual indication of at least said first and second response signals in response to said fourth, fifth, sixth and seventh signals.

10. An acoustic coupling device for a hearing screening device adapted to test the hearing of a subject, said hearing screening device being adapted to provide an acoustic stimulus, said acoustic coupling device comprising:

engagement means for engaging said hearing screening device, said engagement means being adapted to receive said acoustic stimulus and transmit at least one response signal from said subject to said hearing screening device;

stimulus monitoring means in communication with said engagement means for monitoring said acoustic stimulus;

at least a first earpiece adapted to be disposed proximate the cavity of at least one ear of said subject, said earpiece including a stimulus input in communication with said engagement means adapted to receive said acoustic stimulus, said stimulus input being further adapted to receive and transmit said response signal to said engagement means, said earpiece further including a response signal output adapted to receive and transmit said response signal; and response signal monitoring means in communication with said response signal output for monitoring said response signal.

11. An acoustic coupling apparatus for a hearing screening device adapted to test the hearing of a subject, said hearing screening device including means for providing a first acoustic stimulus and means for receiving a first response signal from the subject's first ear and a second response signal from the subject's second ear, comprising:

engagement means for substantially sealably engaging said hearing screening device, said engagement means including at least first and second input members in communication with said means for providing said first acoustic stimulus and means for receiving said first and second response signals, said first and second input members being adapted to receive and transmit at least said first acoustic stimulus and transmit at least said first and second response signals to said hearing screening device;

a first signal generator for providing a second acoustic stimulus, said first signal generator including a first acoustic stimulus output adapted to transmit said second acoustic stimulus;

a second signal generator for providing a third acoustic stimulus, said second signal generator including a second acoustic stimulus output adapted to transmit said third acoustic stimulus;

first monitoring means in communication with said engagement means for monitoring said first acoustic stimulus, said first monitoring means including at least a first acoustic attenuator in communication with said first input member and a second acoustic attenuator in communication with said second input member, said first attenuator being adapted to receive said first acoustic stimulus and provide at least a first signal in response to said first acoustic stimulus, said second attenuator being adapted to receive said first acoustic stimulus and provide at least a second signal in response to said first acoustic stimulus;

regulator means for regulating said second and third acoustic stimuli, said regulator means being in communication with said first and second acoustic attenuators and said first and second signal generators, said regulator means being adapted to provide at least a third signal to said first signal generator in response to said first signal and at least a fourth signal to said second signal generator in response to said second signal, said first signal generator being adapted to provide at least said second acoustic stimulus in response to said third signal, said second signal generator being adapted to provide at least said third acoustic stimulus in response to said fourth signal, second monitoring means for monitoring at least said first and second response signals, said second monitoring means including first response signal input means for receiving said first response signal and second response signal input means for receiving said second response signal, said second monitoring means including a first microphone in communication with said second monitoring means adapted to provide at least a fifth signal to said second monitoring means in response to said first response signal and a second microphone in communication with said second monitoring means adapted to provide at least a sixth signal to said second monitoring means in response to said second response signal; and a first earpiece adapted to be disposed proximate the cavity of said first ear and a second earpiece adapted to be disposed proximate the cavity of said second ear, said first earpiece including a first stimulus input in communication with said first acoustic stimulus output adapted to receive said second acoustic stimulus and said first response signal, said first earpiece further including a first response signal output adapted to receive at least said first response signal, said first response signal output being in communication with said first response signal input means, said second earpiece including a second stimulus input in communication with said second acoustic stimulus output adapted to receive said third acoustic stimulus and said second response signal, said second earpiece further including a second response signal output adapted to receive at least said second response signal, said second response signal output being in communication with said second response signal input means.

12. The apparatus of claim 11, wherein said second acoustic stimulus and said third acoustic stimulus have substantially equal amplitudes.

13. The apparatus of claim 11, wherein said first acoustic attenuator provides at least a first reduction in amplitude of said first acoustic stimulus and said second attenuator provides at least a second reduction in amplitude of said first acoustic stimulus.

14. The apparatus of claim 13, wherein said first and second reductions in amplitude of said first stimulus are substantially equal.

15. The apparatus of claim 11, wherein said apparatus includes control means for controlling at least the activation of said apparatus.

16. The apparatus of claim 15, wherein at least one of said first and second attenuators includes a third microphone to detect the presence of said first acoustic stimulus, said third microphone being adapted to provide at least a seventh signal to said control means in response to said presence of said first acoustic stimulus.

17. The apparatus of claim 11, wherein said second monitoring means provides at least a eighth signal in response to at least said first response signal indicative of an acceptable stimulus amplitude and at least a ninth signal in response to at least said first response signal indicative of an unacceptable stimulus amplitude.

18. The apparatus of claim 17, wherein said second monitoring means provides at least a tenth signal in response to at least said second response signal indicative of an acceptable stimulus amplitude and at least a eleventh signal in response to at least said second response signal indicative of an unacceptable stimulus amplitude.

19. The apparatus of claim 18, wherein said apparatus includes display means in communication with said second monitoring means for providing a visual indication of at least said first and second response signals in response to said eighth, ninth, tenth and eleventh signals.

20. An acoustic coupling device for a hearing screening device adapted to test the hearing of a subject, said hearing screening device being adapted to provide a first acoustic stimulus, said acoustic coupling device comprising:

engagement means for engaging said hearing screening device, said engagement means being adapted to receive said first acoustic stimulus and transmit at least one response signal from said subject to said hearing screening device;

stimulus monitoring means in communication with said engagement means for monitoring said first acoustic stimulus;

stimulus regulator means in communication with said stimulus monitoring means for providing a second acoustic stimulus in response to said first acoustic stimulus;

at least a first earpiece adapted to be disposed proximate the cavity of at least one ear of said subject, said earpiece including a stimulus input in communication with said engagement means and said stimulus regulator means adapted to receive said second acoustic stimulus, said stimulus input being further adapted to receive and transmit said response signal to said engagement means, said earpiece further including a response signal output adapted to receive and transmit said response signal; and response signal monitoring means in communication with said response signal output for monitoring said response signal.

* * * * *